United States Patent
Murase

(10) Patent No.: US 10,473,611 B2
(45) Date of Patent: Nov. 12, 2019

(54) ELECTROCHEMICAL SENSOR AND METHOD FOR PRODUCING ELECTROCHEMICAL SENSOR

(71) Applicant: ARKRAY, Inc., Kyoto (JP)

(72) Inventor: Yosuke Murase, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 76 days.

(21) Appl. No.: 14/886,798

(22) Filed: Oct. 19, 2015

(65) Prior Publication Data

US 2016/0116429 A1    Apr. 28, 2016

(30) Foreign Application Priority Data

Oct. 22, 2014   (JP) .................. 2014-215410
Sep. 24, 2015   (JP) .................. 2015-186817

(51) Int. Cl.
| | |
|---|---|
| *G01N 27/30* | (2006.01) |
| *H05K 1/09* | (2006.01) |
| *G01N 27/40* | (2006.01) |
| *A61B 5/1486* | (2006.01) |
| *H05K 1/02* | (2006.01) |
| *H05K 1/03* | (2006.01) |

(52) U.S. Cl.
CPC ......... *G01N 27/40* (2013.01); *A61B 5/14865* (2013.01); *G01N 27/301* (2013.01); *H05K 1/028* (2013.01); *H05K 1/0313* (2013.01); *H05K 1/097* (2013.01)

(58) Field of Classification Search
CPC .... G01N 27/302; G01N 27/40; G01N 27/301; H05K 1/028; H05K 1/0313; H05K 1/097
See application file for complete search history.

(56) References Cited

U.S. PATENT DOCUMENTS

| | | | |
|---|---|---|---|
| 5,063,081 A | | 11/1991 | Cozzette et al. |
| 5,522,978 A | * | 6/1996 | Pace .................. G01N 27/3335 |
| | | | 204/403.06 |
| 6,144,871 A | | 11/2000 | Saito et al. |
| 2001/0032785 A1 | | 10/2001 | Cha et al. |
| 2009/0294284 A1 | | 12/2009 | Hsiung et al. |

FOREIGN PATENT DOCUMENTS

| | | |
|---|---|---|
| EP | 0 643 299 A1 | 3/1995 |
| EP | 2293054 A1 | 3/2001 |
| JP | H07198670 A | 8/1995 |
| JP | H11281609 A | 10/1999 |

(Continued)

OTHER PUBLICATIONS

Moussy et al, "Prevention of the Rapid Degradation of Subcutaneously Implanted Ag/AgCl Reference Electrodes Using Ploymer Coatings", Analytical Chemistry, vol. 66, No. 5, p. 674-679, Mar. 1, 1994.

(Continued)

*Primary Examiner* — Bethany L Martin
(74) *Attorney, Agent, or Firm* — Studebaker & Brackett PC

(57) ABSTRACT

An electrochemical sensor includes a base member, a conductor disposed on the base member, an insulating layer covering the conductor with a portion of the conductor exposed, a silver/silver chloride electrode formed on at least the exposed portion of the conductor, and a water-permeable organic layer covering the silver/silver chloride electrode.

6 Claims, 4 Drawing Sheets

(56) References Cited

FOREIGN PATENT DOCUMENTS

JP            3104672 B2     10/2000
JP            2013238398 A     11/2013

OTHER PUBLICATIONS

The extended European search report issued by the European Patent Office dated Mar. 29, 2016, which corresponds to European Patent Application No. 15190563.5-1554 and is related to U.S. Appl. No. 14/886,798.

M. B. Andrade Fontes et al.; "Microelectrode Array for Cardiac Potential Mapping"; XVI International Conference on Microelectronics and Packaging—SBMicro2001; Sep. 14, 2001; San Paulo, Brazil.

M. W. Shinwari et al.; "Microfabricated Reference Electrodes and their Biosensing Applications"; Sensors; Mar. 2, 2010; vol. 10; No. 3; pp. 1679-1715.

R. M. Pemberton et al.; "Fabrication and Evaluation of a Micro(Bio)Sensor Array Chip for Multiple Parallel Measurements of Important Cell Biomarkers"; Sensors; Oct. 30, 2014; vol. 14; No. 11; pp. 20519-20532.

Communication pursuant to Article 94(3) EPC issued by the European Patent Office dated Dec. 2, 2016, which corresponds to European Patent Application No. 15190563.5-1554 and is related to U.S. Appl. No. 14/886,798.

T. Matsumoto et al.; "Development of a micro-planar Ag/AgCl quasi-reference electrode with long-term stability for an amperometric glucose sensor"; Analytica Chimica Acta; 2002; pp. 253-259; vol. 462; Elsevier.

An Office Action mailed by the Japanese Patent Office dated Mar. 5, 2019, which corresponds to Japanese Patent Application No. 2015-186817 and is related to U.S. Appl. No. 14/886,798; with English translation.

An Office Action mailed by the European Patent Office dated May 29, 2019, which corresponds to European Patent Application No. 15190563.5 and is related to U.S. Appl. No. 14/886,798.

Shaw-Hwa Parng et al., "Effect of temperature and glucose concentration on a glass-based sensor for long-term stability investigation", Journal of Micro/Nanolithography, MEMS MOEMS, vol. 10, No. 1, Jan.-Mar. 2011, pp. 013003-1 to 013003-5.

EP Office Action dated Jul. 25, 2017, Communication pursuant to Article 94(3) EPC, from corresponding EP Appl No. 15 190 563.5, 6 pp.

An Office Action, issued by the European Patent Office dated Jan. 25, 2018, which corresponds to European Patent Application No. 15190563.5 and is related to U.S. Appl. No. 14/886,798.

\* cited by examiner

ELECTROCHEMICAL SENSOR AND METHOD FOR PRODUCING ELECTROCHEMICAL SENSOR

CROSS-REFERENCE TO RELATED APPLICATION

This application claims the benefit of Japanese Patent Application No. 2014-215410 filed on Oct. 22, 2014 and No. 2015-186817 filed on Sep. 24, 2015 in the Japanese Patent Office, the disclosure of which is herein incorporated in its entirety by reference.

FIELD

The disclosure relates to an electrochemical sensor and a method for producing an electrochemical sensor.

BACKGROUND

A compact electrochemical sensor such as a glucose sensor includes a reference electrode in addition to a working electrode and a counter electrode in many cases. In such an electrochemical sensor, a silver/silver chloride electrode (Ag/AgCl electrode) is generally used as the reference electrode.

[Patent document 1] Japanese Patent No. 3104672

A silver/silver chloride electrode of an electrochemical sensor is formed, for example, on an underlying electrode provided on a base member of the electrochemical sensor. Each of electrodes (a working electrode, a counter electrode and the underlying electrode) of a recent electrochemical sensor has a very small size. Besides, a distance between the electrodes is also small, and therefore, it is difficult to form, in a recent electrochemical sensor, a silver/silver chloride electrode so as not to cause a short circuit. Furthermore, when measurement is performed with the electrochemical sensor for a long period of time, there arises a problem in which the potential of the reference electrode is not stable due to elution of silver/silver chloride.

Accordingly, an object of an embodiment of the present invention is to provide a technique in which a margin regarding the range or the position of forming a silver/silver chloride electrode may be increased, and in which elution of silver/silver chloride is suppressed to stabilize the potential of the silver/silver chloride electrode (reference electrode).

SUMMARY

In order to solve the above-described problems, an electrochemical sensor of an embodiment of the present invention includes: a base member; a conductor disposed on the base member; an insulating layer covering the conductor with a portion of the conductor exposed; a silver/silver chloride electrode formed at least on the exposed portion of the conductor; and a water-permeable organic layer covering the silver/silver chloride electrode.

Specifically, on the conductor (and the base member) of the electrochemical sensor of the embodiment of the present invention, the insulating layer covering the conductor with a portion of the conductor exposed is provided. Accordingly, in the electrochemical sensor of an embodiment of the present invention, a short circuit through the silver/silver chloride electrode does not occur unless the silver/silver chloride electrode protrudes beyond the insulating layer in forming the silver/silver chloride electrode. Besides, since the insulating layer covering the conductor with the portion of the conductor exposed is larger than the conductor, when the structure of the embodiment of the present invention is employed, an electrochemical sensor in which a margin regarding the range or the position of forming a silver/silver chloride electrode is larger than in an electrochemical sensor in which no insulating layer is provided on a conductor may be obtained. Furthermore, the electrochemical sensor of the embodiment of the present invention includes the water-permeable organic layer covering the silver/silver chloride electrode. Therefore, in the electrochemical sensor of the embodiment of the present invention, elution of silver/silver chloride is suppressed by the organic layer, and hence, the potential of the silver/silver chloride electrode serving as a reference electrode is stabilized.

Besides, when the electrochemical sensor of the embodiment of the present invention is constituted (produced) as one including the silver/silver chloride electrode formed on the exposed portion of the conductor and on the insulating layer, since the amount of the silver/silver chloride electrode within the sensor is larger than in an electrochemical sensor in which no insulating layer is provided on a conductor, the resultant sensor attains a longer life.

The shape of the insulating layer of the electrochemical sensor of the embodiment of the present invention may be a shape covering merely the vicinity of the "exposed portion of the conductor" as long as another electrode (a working electrode or a counter electrode) disposed on the base member is not excessively covered. However, as the size of the insulating layer is larger, the silver/silver chloride electrode is formed more easily, and the silver/silver chloride electrode having a larger size may be formed on the insulating layer. Accordingly, the shape of the insulating layer is preferably determined to make a width of each portion of the insulating layer as large as possible under conditions that the insulating layer does not cover another electrode (or does not excessively cover another electrode).

The organic layer of the electrochemical sensor of the embodiment of the present invention may be a water-permeable organic layer, and is preferably a limiting film that suppresses diffusion and elution of a silver ion and/or a silver chloride complex in an external solution. Besides, the limiting film may be a film of a polymer having a hydrophilic group (such as a hydroxyl group, a carboxyl group, a sulfonic group or an amino group). Incidentally, it may be determined on the basis of the use, the specific structure and the like of the electrochemical sensor how water-permeable the organic layer to be employed is.

Besides, in order to solve the above-described problems, a method for producing an electrochemical sensor of the embodiment of the present invention includes: forming a structure including a base member, a conductor disposed on the base member, and an insulating layer covering the conductor with a portion of the conductor exposed; forming a silver/silver chloride electrode on the structure in such a manner as to be in contact with at least the exposed portion of the conductor; and forming a water-permeable organic layer covering the silver/silver chloride electrode.

Specifically, the method for producing an electrochemical sensor of the embodiment of the present invention includes the forming, on a "structure including a base member, a conductor disposed on the base member, and an insulating layer covering the conductor with a portion of the conductor exposed", a silver/silver chloride electrode in such a manner as to be in contact with at least the exposed portion of the conductor. Besides, when this forming is employed, a short circuit through the silver/silver chloride electrode does not occur unless the silver/silver chloride electrode protrudes beyond the insulating layer of the "structure". Accordingly, when the method for producing an electrochemical sensor of the embodiment of the present invention is employed, an electrochemical sensor may be produced with a larger margin regarding the range or the position of forming the silver/silver chloride electrode than in production of an electrochemical sensor including no insulating layer provided on a conductor. Besides, when the method for producing an electrochemical sensor of the embodiment of the present invention is employed, an electrochemical sensor including a larger amount of silver/silver chloride electrode may be more easily produced than in the production of an electrochemical sensor including no insulating layer provided on a conductor. Furthermore, an electrochemical sensor produced by the method for producing an electrochemical sensor of the embodiment of the present invention includes a water-permeable organic layer covering the silver/silver chloride electrode. Therefore, in the electrochemical sensor produced by the method for producing an electrochemical sensor of the embodiment of the present invention, elution of silver/silver chloride is suppressed by the organic layer, and hence the potential of the silver/silver chloride electrode serving as a reference electrode is stabilized.

The "forming a silver/silver chloride electrode" of the method for producing an electrochemical sensor of the embodiment of the present invention may be performed with any contents/procedures. However, when applying a silver/silver chloride ink on the structure is employed to be included in this forming, the silver/silver chloride electrode may be formed more easily than in a case where another process (for example, a process including formation of a mask layer, vacuum deposition, or the like) is employed.

Besides, the silver/silver chloride electrode of the electrochemical sensor of the embodiment of the present invention has a structure in which it is formed in such a manner as to be in contact with the exposed portion of the conductor covered with the insulating layer and is covered with the organic layer. Accordingly, the silver/silver chloride electrode of the electrochemical sensor of the embodiment of the present invention is an electrode having a large margin regarding the range or the position of forming it.

According to the embodiment of the present invention, a technique in which a margin regarding the range or the position of forming a silver/silver chloride electrode may be increased, and in which elution of silver/silver chloride is suppressed to stabilize the potential of the silver/silver chloride electrode may be provided.

DESCRIPTION OF EMBODIMENTS

Now, the structure of an electrochemical sensor according to one embodiment of the present invention will be described together with production procedures. Incidentally, the electrochemical sensor described as the embodiment of the present invention below is a sensor whose tip portion is inserted under the skin of a belly, a shoulder or the like of a human body for continuously measuring a concentration of glucose in a blood or a subcutaneous interstitial fluid. However, a structure of the embodiment of the present invention relating to a reference electrode (a silver/silver chloride electrode) is applicable to any electrochemical sensor including a silver/silver chloride electrode regardless of its use.

Figure 1:
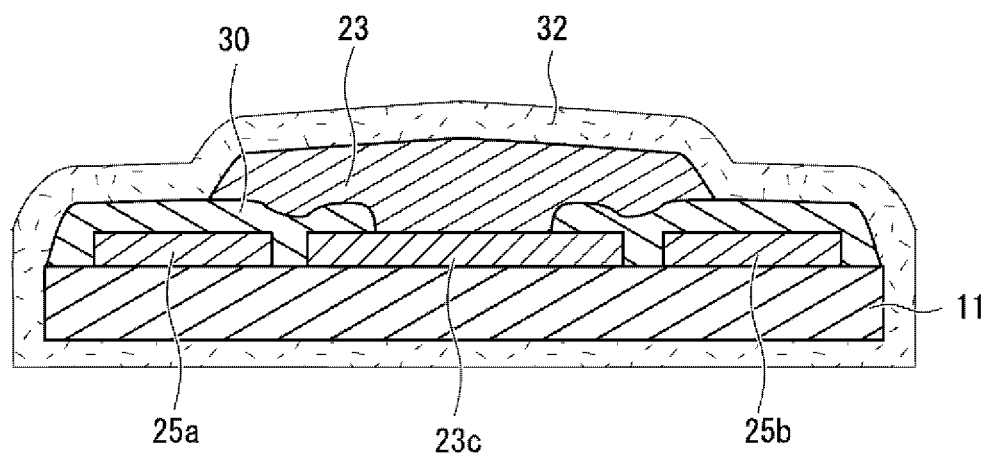
FIG. 1 is a cross-sectional view, in parallel to a widthwise direction of a substrate, of a part of an electrochemical sensor according to an embodiment in which a silver/silver chloride electrode is provided.
Figure 2:
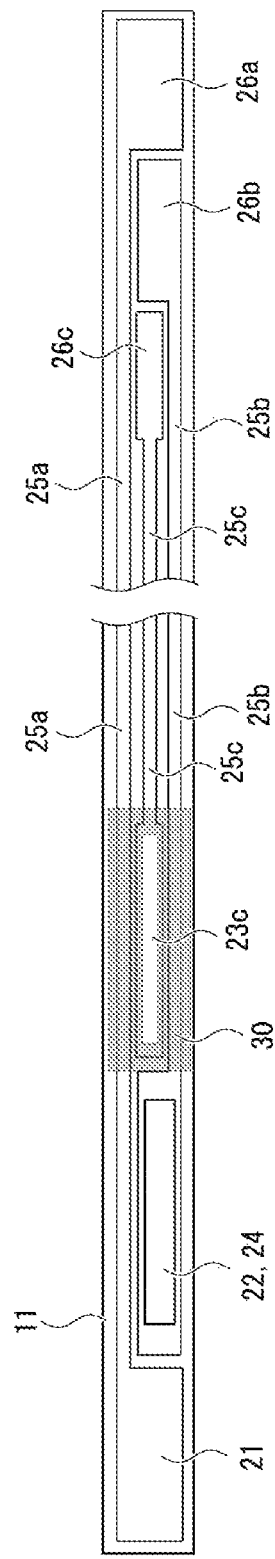
FIG. 2 is a plan view of a sensor structure formed in a production procedure of the electrochemical sensor of the embodiment.

FIG. 1 illustrates a cross-sectional view, in parallel to a widthwise direction of a base member 11, of a portion of the electrochemical sensor of the present embodiment in which a silver/silver chloride electrode 23 is provided, and FIG. 2 illustrates a plan view of a sensor structure formed in a production procedure of the electrochemical sensor of the present embodiment.

The electrochemical sensor (see FIG. 1) of the present embodiment is produced by forming the silver/silver chloride electrode 23 on an underlying electrode 23c and an insulating layer 30 of the sensor structure illustrated in FIG. 2, and then forming an organic layer 32 at least covering the silver/silver chloride electrode 23.

First, the sensor structure (FIG. 2) will be described. As illustrated in the drawing, the sensor structure includes the long and narrow base member 11, and a counter electrode 21, a working electrode 22 and the underlying electrode 23c formed on one end portion of the base member 11. Besides, the sensor structure includes an enzyme reagent layer 24 formed on the working electrode 22, and contact pads 26a through 26c formed on the other end portion of the base member 11. Furthermore, the sensor structure includes a wiring 25a electrically connecting between the contact pad 26a and the counter electrode 21, a wiring 25b electrically connecting between the contact pad 26b and the working electrode 22, and a wiring 25c electrically connecting between the contact pad 26c and the underlying electrode 23c, all formed on the base member 11.

Each contact pad 26x (x=a to c) of the sensor structure is a terminal to be connected, in use of the electrochemical sensor obtained after completion of the production, to a corresponding terminal provided on a measuring apparatus for the electrochemical sensor. Incidentally, in the use of the electrochemical sensor, a potential between the contact pads 26a and 26c is generally controlled to detect an amount of a current flowing between the contact pads 26a and 26b.

The underlying electrode 23c is a conductor formed on the base member 11 as an underlying electrode of the silver/silver chloride electrode 23 (FIG. 1). As illustrated in FIG. 1 and FIG. 2, the insulating layer 30 covering the underlying electrode 23c with a portion of the underlying electrode 23c exposed is provided on the underlying electrode 23c of the sensor structure (the electrochemical sensor).

This insulating layer 30 may be any layer as long as it is larger than the underlying electrode 23c (sufficiently large to cover the underlying electrode 23c with a portion of the underlying electrode 23c exposed). Accordingly, the insulating layer 30 may be slightly larger than the underlying electrode 23c, but as described above, in the electrochemical sensor of the present embodiment, the silver/silver chloride electrode 23 (FIG. 1) is formed on the underlying electrode 23c and the insulating layer 30. Besides, as the insulating layer 30 has a larger size, the silver/silver chloride electrode 23 may be more easily formed, and the silver/silver chloride electrode 23 in a larger size may be formed on the insulating layer 30. Accordingly, the insulating layer 30 may have a larger size, but it is not preferred that an adjacent electrode of the underlying electrode 23c (the working electrode 22 in FIG. 2) is covered with the insulating layer 30.

Therefore, the shape of the insulating layer 30 is preferably determined to have a width of each portion of the insulating layer 30 as large as possible under conditions that the insulating layer 30 does not cover the adjacent electrode of the underlying electrode 23c (or does not excessively cover the adjacent electrode). Incidentally, the width of each portion of the insulating layer 30 refers to a distance (an interval) between an opening of the insulating layer 30 (through which the underlying electrode 23c is exposed) and an outer edge of the insulating layer 30.

As the constituent material of the base member 11 of the sensor structure, a material having appropriate insulating property and flexibility and having no harmful effect on the human body, for example, a thermoplastic resin, such as PET (polyethylene terephthalate), PP (polypropylene) or PE (polyethylene), may be used. Alternatively, as the constituent material of the base member 11, a thermosetting resin such as a polyimide resin or an epoxy resin may be used.

Besides, as the constituent material of the insulating layer 30, a material from which a thin film having an insulating property may be easily formed, for example, Parylene (a registered trademark of Parylene Japan) may be used.

A portion on the base member 11 including the counter electrode 21, the wiring 25a and the contact pad 26a may be a conductive pattern itself formed from a conductive material such as a metal (for example, Au (gold)), or such a conductive pattern having another conductive material layer formed on a part thereof. Each of portions on the base member 11 respectively including the working electrode 22, the wiring 25b and the contact pad 26b and including the underlying electrode 23c, the wiring 25c and the contact pad 26c may be a conductive pattern itself as described above, or such a conductive pattern having another conductive material layer formed on a part thereof.

The enzyme reagent layer 24 provided on the working electrode 22 is a layer on which a glucose oxidation/reduction enzyme is immobilized. As the glucose oxidation/reduction enzyme, GOD (glucose oxidase) or GDH (glucose dehydrogenase) may be used. Besides, as an immobilization method for the glucose oxidation/reduction enzyme, any of known methods may be employed. Specifically, as the immobilization method for the glucose oxidation/reduction enzyme, a method using a polymer such as a polymerizable gel, polyacrylamide or phosphorus, a method using an MPC polymer obtained by binding a phospholipid polymer with a silane coupling agent, or a method using a protein coating may be employed.

Next, the silver/silver chloride electrode 23 and the organic layer 32 will be described.

The silver/silver chloride electrode 23 is silver/silver chloride (a mixture of silver and silver chloride) formed, as a reference electrode, on at least the exposed portion of the underlying electrode 23c. The forming process of this silver/silver chloride electrode 23 may be any process. For example, the silver/silver chloride electrode 23 may be formed by applying a silver/silver chloride ink on the sensor structure by screen printing.

Besides, the size of the silver/silver chloride electrode 23 may be a size substantially equivalent to that of the underlying electrode 23c. However, in the electrochemical sensor of the present embodiment, a short circuit does not occur unless the silver/silver chloride electrode 23 protrudes beyond the insulating layer 30. Besides, as the amount of the silver/silver chloride electrode 23 within the electrochemical sensor is larger, the life of the electrochemical sensor is longer. Therefore, the size of the silver/silver chloride electrode 23 is preferably larger than the size of the underlying electrode 23c. It is noted that the upper limit of the size of the silver/silver chloride electrode 23 may be obtained on the basis of the positional accuracy in the forming process of the silver/silver chloride electrode 23 and the size of the insulating layer 30.

The organic layer 32 may be any water-permeable organic layer, and is preferably a limiting film that suppresses the diffusion and elution of a silver ion and/or a silver chloride complex to an external solution. Besides, the organic layer 32 may be a film of a polymer having a hydrophilic group such as a hydroxyl group, a carboxyl group, a sulfonic group or an amino group, or a porous film of a polymer not having a hydrophilic group. Incidentally, it may be determined on the basis of the use, the specific structure and the like of the electrochemical sensor how water-permeable the organic layer to be employed as the organic layer 32 is.

Furthermore, the organic layer 32 may be one covering the silver/silver chloride electrode 23 and a surrounding portion alone, or one covering an entire tip portion of the electrochemical sensor (see FIG. 1). Incidentally, although the electrochemical sensor including no other layer present on the organic layer 32 is illustrated in FIG. 1, it is not necessary for the organic layer 32 to have no other layer present thereon, and hence, another layer, for example, an outer layer film for restricting transmission of a substrate (glucose), may be provided on the organic layer 32.

Now, the function of the electrochemical sensor of the present embodiment will be described in more detail on the basis of Examples 1 to 3 and Comparative Example 1. Incidentally, an electrochemical sensor according to each of Examples 1 to 3 and Comparative Example 1 described below was produced mainly for evaluating the function of the organic layer 32. In the electrochemical sensor of each example, the silver/silver chloride electrode 23 and a surrounding portion alone are covered with the organic layer 32, and in the electrochemical sensor of each of Examples 2 and 3, the organic layer 32, the working electrode and the counter electrode are covered with an external layer film for restricting the transmission of a substrate.

EXAMPLE 1

First, Au (gold) was formed by sputtering on a polyether imide base member used as a base member 11. Subsequently, the Au film on the base member 11 was laser trimmed to form, on the base member 11, an underlying electrode 23c, a wiring 25c, a contact pad 26c and the like. Thereafter, the base member 11 having the underlying electrode 23c and the like formed thereon was coated with Parylene (a registered trademark of Parylene Japan). Next, the Parylene was patterned by dry etching performed after attaching a photoresist, and thus, an insulating layer 30 was formed in a shape for exposing 0.04 mm$^2$ of the underlying electrode 23c.

Thereafter, a silver/silver chloride ink (Gwent Electronic Materials C2121101D1 (a product under development)) was applied, by screen printing, on a region of 0.06 mm$^2$ including the above-described region of 0.04 mm$^2$ of the underlying electrode 23c, and thus, a sensor in which a silver/silver chloride electrode 23 was formed on the underlying electrode 23c and the insulating layer 30 was obtained. Then, Nafion (a registered trademark of DuPont), that is, a proton exchange resin, was applied, with a syringe, on the silver/silver chloride electrode 23 of the sensor, and thus, an electrochemical sensor of Example 1 including a Nafion layer as an organic layer 32 was obtained.

EXAMPLE 2

An electrochemical sensor of Example 2 was produced by performing the following processing (steps) on a sensor in which the silver/silver chloride electrode 23 had been formed through procedures described above.

First, 40 nL (nanoliter) of a water dispersed polyester/crosslinking agent mixture was applied, with a syringe, on the silver/silver chloride electrode 23. The used water dispersed polyester/crosslinking agent mixture was an aqueous solution of Vilonal and Epocros including Vilonal MD-1200 at a final concentration of 1.67% and Epocros WS-700 at a final concentration of 3.33%.

Subsequently, as a crosslinking step of the water dispersed polyester/crosslinking agent mixture, a step of treating the sensor, in which the mixture had been applied, at 60° C. for 60 hours and at 100° C. for 2 hours was performed. Then, in order to form an external layer film for restricting the transmission of a substrate (glucose), the sensor having been subjected to the crosslinking step was dip coated with a 3.5% cellulose acetate solution, and the resultant sensor was dried at 100° C. for 30 minutes. Incidentally, a take-up speed employed in the dip coating was 0.8 mm/sec.

The electrochemical sensor of Example 2 is a sensor including the organic layer 32 and the external layer film for restricting the transmission of a substrate obtained through the aforementioned series of processes.

EXAMPLE 3

An electrochemical sensor of Example 3 was produced by performing the following processing on a sensor in which the silver/silver chloride electrode 23 had been formed through procedures described above.

First, 80 nL of a polyacrylic acid and Carbodilite reagent solution was applied, with a syringe, on the silver/silver chloride electrode 23 under environment of 25° C. and a humidity of 40%. The used reagent solution was one obtained by mixing distilled water, a 40% Carbodilite aqueous solution, a 25% ammonia aqueous solution and a 20% polyacrylic acid aqueous solution into final concentrations of Carbodilite, ammonia and polyacrylic acid of 1.60%, 4.0 M and 5.0%, respectively. Incidentally, SV-02 manufactured by Nisshinbo Chemical Inc. was used as the 40% Carbodilite aqueous solution, and polyacrylic acid (Wako 1st Grade) manufactured by Wako Pure Chemical Industries, Ltd. was used as the polyacrylic acid. Besides, the preparation of the reagent solution was performed by mixing, with distilled water, the 40% Carbodilite aqueous solution, the 25% ammonia aqueous solution and the 20% polyacrylic acid aqueous solution in this order.

Then, the silver/silver chloride electrode 23 on which the polyacrylic acid and Carbodilite reagent solution had been applied was allowed to stand still under the above-described environment for about 15 minutes, and the resultant was dried in a low humidity dry box for 24 hours. Subsequently, a heat treatment (crosslinking processing) was performed at 100° C. for 24 hours. Thereafter, in order to form an outer layer film for restricting the transmission of a substrate (glucose), the sensor resulting from the heat treatment was dip coated with a 3.5% cellulose acetate solution, and the resultant sensor was dried at 100° C. for 30 minutes.

COMPARATIVE EXAMPLE 1

An electrochemical sensor of Comparative Example 1 was a sensor in which the silver/silver chloride electrode 23 was formed through the same procedures as those of the electrochemical sensors of Examples 1 and 2 (a sensor not provided with the organic layer 32).

<<Evaluation methods and evaluation results of electrochemical sensors of examples/comparative example>>

The electrochemical sensors of the examples/comparative example produced as described above were evaluated for the stability of a potential of the silver/silver chloride electrode 23 and an elution rate of silver.

Evaluation Method and Evaluation Results of Stability of Potential of Silver/Silver Chloride Electrode 23

Each of the electrochemical sensors of the examples/comparative example produced as described above was immersed in a PBS (Phosphate Buffered Saline) solution at 37° C., and the potential transition of the silver/silver chloride electrode 23 of each sensor was recorded by using a silver/silver chloride electrode (having an internal solution of 3M NaCl) manufactured by BAS Inc. as a reference. Incidentally, the used PBS solution was one containing NaCl, KCl, $Na_2HPO_4$ and $KH_2PO_4$ respectively at concentrations of 137 mM, 1.76 mM, 10 mM and 2.7 mM.

Figure 3:
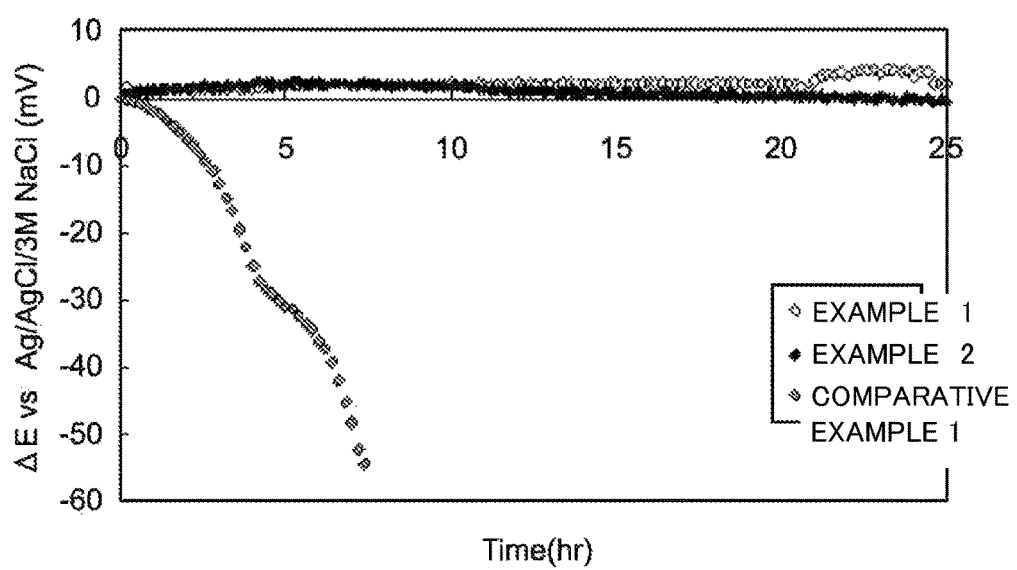
FIG. 3 is a graph illustrating recorded results of potential transition of silver/silver chloride electrodes of electrochemical sensors of Examples 1 and 2 and Comparative Example 1.

FIG. 3 illustrates the recorded results of the potential transition of the silver/silver chloride electrodes 23 of the respective electrochemical sensors. Incidentally, the recorded result of the potential transition of the electrochemical sensor of Example 3 had the same tendency as the recorded result of the potential transition of the electrochemical sensor of Example 1. Therefore, in order to avoid the graph (FIG. 3) from becoming complicated, the recorded result of the potential transition of the electrochemical sensor of Example 3 is omitted in FIG. 3.

As is obvious from FIG. 3, in the electrochemical sensor of Comparative Example 1 in which the organic layer was not provided, potential drift was observed immediately after starting the measurement (recording). On the other hand, in the electrochemical sensors of Examples 1 and 2 (and 3) in which the organic layer 32 was provided, substantially no potential drift was observed, and it was confirmed that the organic layer 32 formed through the above-described procedures is effective to stabilize the potential of the reference electrode (the silver/silver chloride electrode 23) of the electrochemical sensor.

Evaluation Method and Evaluation Results of Elution Rate of Silver

The sensor of each of the examples/comparative example was immersed in 10 mL (milliliter) of a PBS solution at 37° C., and was allowed to stand for 24 hours. Thereafter, the concentration of Ag in the PBS solution was determined by ICP-AES (Inductively Coupled Plasma Atomic Emission Spectroscopy).

The determined results of the Ag concentration in the PBS solution were as follows:

Comparative Example 1: 0.568 mg/L
Example 1: 0.201 mg/L
Example 2: 0.130 mg/L
Example 3: 0.258 mg/L In this manner, it was confirmed that the elution rate of silver from the silver/silver chloride electrode 23 may be reduced to ½ or less by covering the silver/silver chloride electrode 23 with the organic layer 32 formed through the above-described procedures.

As described above, the insulating layer 30 covering the underlying electrode 23c with a portion of the underlying electrode 23c exposed is provided on the underlying electrode 23c and the base member 11 of the electrochemical sensor of the present embodiment. Therefore, a short circuit through the silver/silver chloride electrode 23 does not occur in the electrochemical sensor of the present embodiment unless the silver/silver chloride electrode 23 protrudes beyond the insulating layer 30 in forming the silver/silver chloride electrode 23.

Figure 4:
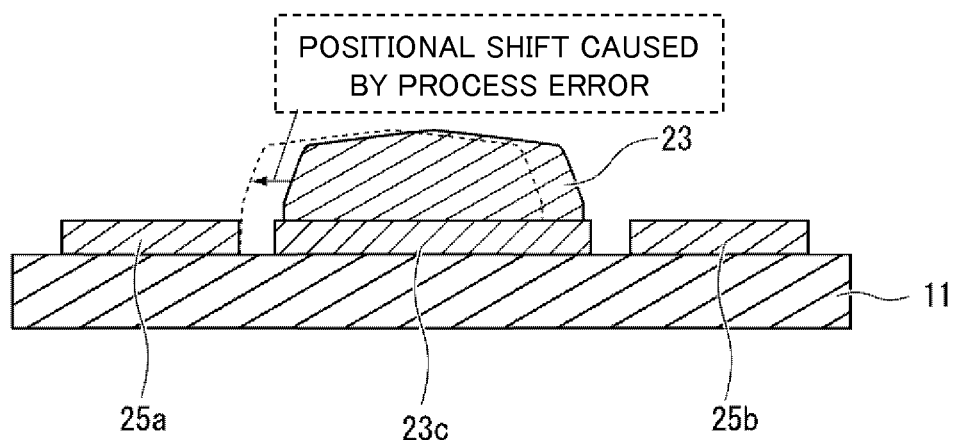
FIG. 4 is an explanatory diagram illustrating a phenomenon occurring when no insulating layer is provided.

On the other hand, when the insulating layer 30 is not provided, a short circuit between the underlying electrode 23c and the wiring 25a is caused through the silver/silver chloride electrode 23 when the position of forming the silver/silver chloride electrode 23 is shifted by a process error merely correspondingly to a distance between the underlying electrode 23c and the wiring 25a as schematically illustrated in FIG. 4.

Besides, as described above, a short circuit through the silver/silver chloride electrode 23 does not occur in the electrochemical sensor of the present embodiment unless the silver/silver chloride electrode 23 protrudes beyond the insulating layer 30. Accordingly, when the structure of the electrochemical sensor of the present embodiment is employed, a sensor having a larger margin regarding the position or the like of forming the silver/silver chloride electrode 23 than in an electrochemical sensor not provided with the insulating layer 30 may be attained. Besides, as is obvious from comparison between FIG. 1 and FIG. 4, when the structure of the electrochemical sensor of the present embodiment is employed, an electrochemical sensor containing a larger amount of the silver/silver chloride electrode 23 therein than in an electrochemical sensor not provided with the insulating layer 30 may be attained.

Furthermore, the water-permeable organic layer 32 is provided on the silver/silver chloride electrode 23 of the electrochemical sensor of the present embodiment. Therefore, in the electrochemical sensor of the present embodiment, the elution of silver/silver chloride is suppressed by the organic layer 32, and hence the potential of the silver/silver chloride electrode 23 (the reference electrode) is stabilized (see FIG. 3).

<<Modifications>>

The electrochemical sensor of the present embodiment described above may be variously modified. For example, the shape of the base member 11 of the sensor structure (the electrochemical sensor), and the shapes of and the positional relationship among the respective portions of the base member 11 may be different from those illustrated in FIG. 2. However, when a structure in which the underlying electrode 23c and the other electrode(s) (the counter electrode 21 and/or the working electrode 22) are arranged along the widthwise direction of the base member 11 is employed, the size of the insulating layer 30 along the widthwise direction of the base member 11 is limited by the presence of the other electrode(s) on the base member 11. Accordingly, when an electrochemical sensor in which the underlying electrode 23c and the other electrode(s) are arranged along the widthwise direction of the base member 11 and an electrochemical sensor in which the respective electrodes are arranged along the lengthwise direction of the base member 11 (see FIG. 2) are produced by using the same base member 11, the size of the insulating layer 30 is unavoidably smaller in the former electrochemical sensor than in the latter electrochemical sensor.

On the other hand, when the respective electrodes are arranged along the lengthwise direction of the base member 11 (FIG. 2), the insulating layer 30 may be formed in a size extending between both long sides of the base member 11 regardless of the position of the underlying electrode 23c. Accordingly, in the sensor structure (the electrochemical sensor), the order of arranging the electrodes may be different from that described above, but the structure in which the respective electrodes are arranged on the base member 11 along the lengthwise direction of the base member 11 is preferably employed.

Besides, although the electrochemical sensor of the present embodiment described above includes the counter electrode 21, the working electrode 22 and the silver/silver chloride electrode 23 serving as the reference electrode, the counter electrode 21 may be omitted to allow the silver/silver chloride electrode 23 to serve as the reference electrode and the counter electrode 21.

Furthermore, as the constituent materials of the respective portions, materials different from those described above may be used. For example, the organic layer 32 may be any film having water permeability. Accordingly, a material different from those described above (for example, polyurethane, polyamide or the like) may be used as the constituent material of the organic layer 32. Besides, it goes without saying that an electrochemical sensor not for measuring a glucose concentration may be produced on the basis of the above-described technique.

What is claimed is:

1. An electrochemical sensor comprising:
   a base member;
   a first conductor disposed on the base member;
   a second conductor neighboring the first conductor;
   an insulating layer covering the first conductor to form an exposed portion of the first conductor;
   a silver/silver chloride electrode formed at least on the exposed portion of the first conductor; and
   a water-permeable organic layer covering the silver/silver chloride electrode and having an outer layer film including cellulose acetate, wherein
   the insulating layer covers the second conductor and the first conductor except for the exposed portion, and the insulating layer insulates between the first conductor and the second conductor,
   the silver/silver chloride electrode is formed on the exposed portion and on the insulating layer, and
   the silver/silver chloride electrode has an edge that extends over the second conductor.

2. The electrochemical sensor according to claim 1, wherein the organic layer is a limiting film that restricts transmission of a component eluted from the silver/silver chloride.

3. The electrochemical sensor according to claim 2, wherein the limiting film is a film of a polymer having a hydrophilic group.

4. An electrochemical sensor comprising:
   a base member;
   a first conductor disposed on a surface of the base member;
   a second conductor neighboring the first conductor;
   an insulating layer covering the first conductor to form an exposed portion of the first conductor;
   a silver/silver chloride electrode formed at least on the exposed portion of the first conductor and over a part of the insulating layer in a direction perpendicular to and extending away from the surface of the base member; and
   a water-permeable organic layer covering the silver/silver chloride electrode and having an outer layer film including cellulose acetate, wherein the insulating layer covers the second conductor and the first conductor except for the exposed portion, and the insulating layer insulates between the first conductor and the second conductor, the silver/silver chloride electrode is formed on the exposed portion and on the insulating layer, and the silver/silver chloride electrode has an edge that extends over the second conductor.

5. The electrochemical sensor according to claim 4, wherein the organic layer is a limiting film that restricts transmission of a component eluted from the silver/silver chloride.

6. The electrochemical sensor according to claim 5, wherein the limiting film is a film of a polymer having a hydrophilic group.

* * * * *